United States Patent
Bowers

(10) Patent No.: US 6,319,261 B1
(45) Date of Patent: Nov. 20, 2001

(54) ELECTROHYDRAULIC LITHOTRIPSY BASKET

(75) Inventor: David Bowers, Lakeland, FL (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/045,523

(22) Filed: Mar. 20, 1998

(51) Int. Cl.[7] .................................................. A61B 17/22
(52) U.S. Cl. ............................................................ 606/127
(58) Field of Search ........................... 606/2.5, 127, 128; 604/27, 127

(56) References Cited

U.S. PATENT DOCUMENTS

| | | |
|---|---|---|
| 1,612,697 | 12/1926 | Cecil . |
| 4,030,505 | 6/1977 | Tessler . |
| 4,046,150 | 9/1977 | Schwartz et al. . |
| 4,203,429 | 5/1980 | Vasilevsky et al. . |
| 4,905,691 | 3/1990 | Rydell . |
| 4,927,427 * | 5/1990 | Kriauciunas et al. ............... 606/128 |
| 5,176,688 | 1/1993 | Narayan et al. . |
| 5,397,320 | 3/1995 | Essig et al. . |

* cited by examiner

Primary Examiner—Michael H. Thaler
Assistant Examiner—Vy Q. Bui
(74) Attorney, Agent, or Firm—Cowen, Liebowitz & Latman, P.C.; William H. Dippert

(57) ABSTRACT

The present invention concerns a novel combination device for the destruction of calculi such as urinary stones in the human bladder, individual urinary ureters, the biliary tract, or other locations in the human body. More specifically, the present invention concerns an electrohydraulic lithotripsy basket (EHL) which consists of multiple electrical conduit wires that act both as electrical conduits and collectively act as a grasping device. This invention also concerns a method for the destruction of urinary stones using the device claimed.

16 Claims, 2 Drawing Sheets

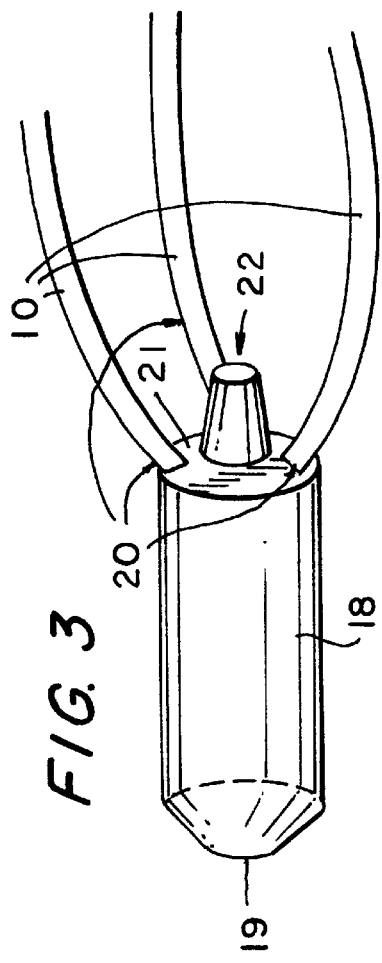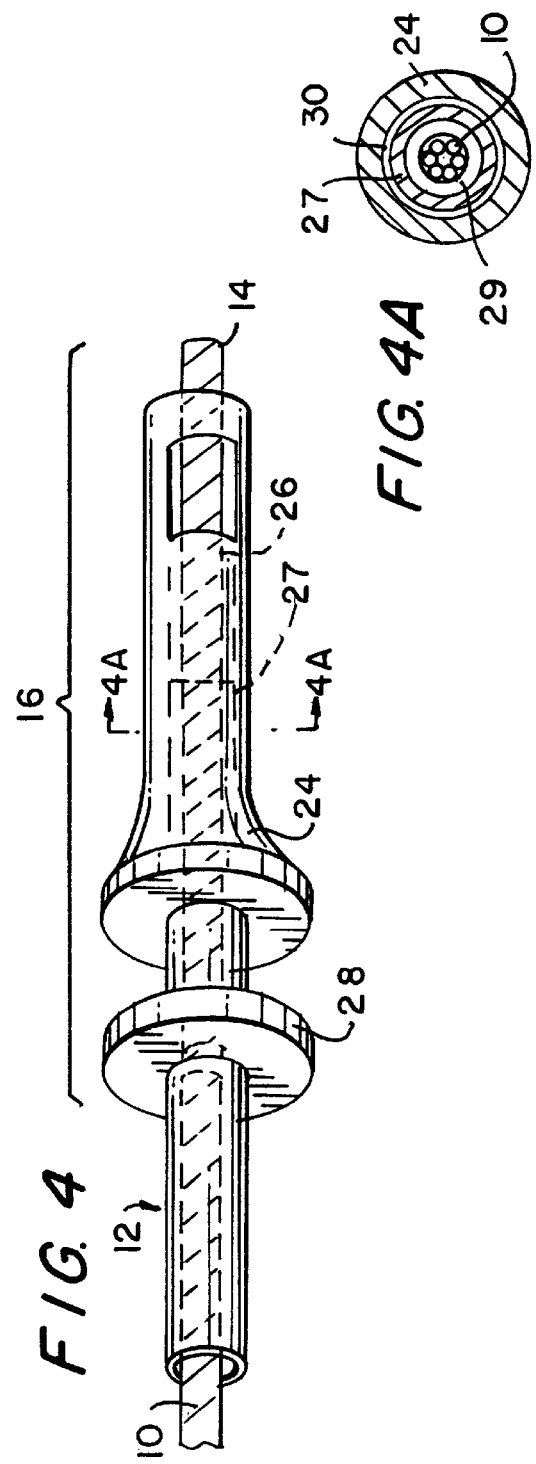

ELECTROHYDRAULIC LITHOTRIPSY BASKET

FIELD OF THE INVENTION

The present invention relates to a novel combination device for the destruction of urinary stones in the human bladder and within the individual ureters. More specifically, the present invention relates to an electrohydraulic lithotripsy basket which consists of multiple electrical conduit wires that act both as electrical conduits and collectively act as a grasping device.

BACKGROUND OF THE INVENTION

Electrohydraulic lithotripsy (EHL) has been an accepted form of therapy for the destruction of urinary stones both in the human bladder and within the individual ureters. Basket extraction of stones is an alternative form of therapy in selected instances. Both urinary stones and biliary stones can be removed by the use of wire basket extraction devices. The choice of the use of either EHL or basket extraction lies in the size and location of the stone, as well as the experience and preference of the urologist. EHL is extremely effective in breaking large urinary stones into pieces small enough for basket extraction or simple passage.

When EHL is selected to affect the destruction of the stone, the EHL probe is placed in close proximity to the stone. By means of an electrical discharge, a shock wave is produced which impacts the surface of the stone and produces tiny cracks. When enough cracks have been made, the stone shatters into small pieces. The individual pieces can then be attacked one at a time, or they can be removed by basket extraction.

Several problems are inherent in EHL. First, EHL is a procedure that requires direct vision to properly place the probe against the stone. And second, there is the danger of perforation of the ureter or bladder during dilation of the ureter orifice or positioning of the cystoureteroscope. The entire time the cystoureteroscope is within the ureter there is also a constant risk of perforation of the ureter.

Further, when the EHL procedure is performed in the ureter, the force of the discharge can propel the stone or its fragments into the delicate lining of the ureter and even perforate the structure. Should the impact point be misdetermined, the discharge of the EHL probe can damage the ureter. Every time the EHL probe fires, the stone moves its position. Therefore, each time the probe is fired, it must be replaced manually on the surface of the stone which is now in a different position. This manual replacement is both time consuming and potentially dangerous.

The device which is the subject of the present invention is designed to combine both a basket extraction device and an EHL probe into a single combination device that will allow a secure hold on a urinary or binary stone while the destructive forces of the EHL probe are used to shatter the stone. The novel combination device of the present invention allows for a safer and faster removal of calculi that was previously not available in the art. Faster, because a single device is used to affect both destruction and extraction of the residual stone fragments, and safer, because this device can be made as small as the smallest wire extraction basket available on the market. In addition, the device of the present invention does not require changing devices in the middle of the procedure, within the very restrictive confines of the urinary or binary tract.

There are a number of prior art references, each of which is directed to some specific discreet element of the system of the present invention; however, none of these references is directed to the totality of the combination, or its use and function in the manner described and claimed herein.

Cecil, U.S. Pat. No. 1,612,697, teaches improvements in instruments for removing and crushing ureteral calculi. In this connection it relates more particularly to the novel arrangement and construction of the parts thereof.

Tessler, U.S. Pat. No. 4,030,505, relates to a method for removing concretions within human ducts, particularly the ureter and kidney, comprising axially abutting a concretion within a human duct, while outwardly distending the walls of the duct adjacent the concretion; generating a series of high voltage electrical pulses of sufficiently low amperage to avoid harm to human tissues; directing said pulses within an insulating medium extending to said ducts to the situs of said concretions; selectively discharging said pulses radially outwardly across the surface of said concretions; and flowing a liquid peripherally of said discharging of pulses, so as to direct a hydroelectric impact against said concretions and within the distended duct walls.

Schwartz et al., U.S. Pat. No. 4,046,150, describes an instrument useful for locating and removing ureteral calculi and other occlusive objects from body passages. The instrument includes a flexible tube or sheath which slidably receives a tightly-twisted multi-stranded cable of a length greater than that of the tube, the cable having an integral cage portion at its distal end. The cage portion, which is normally collapsed and concealed within the distal end of the tube, may be extended beyond the tube to assume an expanded helical pear-shaped configuration for ensnaring and withdrawing ureteral stones and other passage-occluding bodies.

Vasilevsky et al., U.S. Pat. No. 4,203,429, concerns a method of removing concretions from the ureter which comprises passing a concretion from the ureter into the bladder by means of an extractor having a guiding rod at the end of wire arms, crushing the concretion in the bladder by means of a disintegrating instrument, inserting a catheter into the ureter, and removing concretion fragment after the catherization is over.

Rydell, U.S. Pat. No. 4,905,691, is concerned with a polypectome snare whose loop comprises a pair of electrodes mechanically joined but electrically insulated from one another at their distal ends and adapted to be energized by a source of RF voltage for excising polyps on the inside of a body cavity.

Narayan et al., U.S. Pat. No. 5,176,688, teaches an instrument and method for removing stones (calculi) from the kidneys, the bladder and other parts of the body. A stone is captured in a basket at the distal end of an elongated tubular member and broken into pieces while it is held by the basket. The stone is broken up by a hammering action provided by a reciprocating shaft which extends through the tubular member into the basket and is driven toward the stone by a spring.

Essig et al., U.S. Pat. No. 5,397,320, relates to a laparoscopic surgical device which comprises an elongate shaft having a plurality of electrically conductive flexible ribs connected to the distal end of the shaft and to one another to form a cage or basket. Upon placement of an organic body in the cage, the ribs are electrically energized. The organic body is pressed against the ribs to dissect the ribs in a single cauterization operation.

OBJECTS OF THE INVENTION

It is an object of the present invention to provide for a novel combination device for securing calculi and to affect their destruction.

It is also an object of the present invention to provide for a novel combination device to secure calculi and affect their destruction by means of shock waves produced by an electrohydraulic lithotripsy device which is capable of being safely introduced into the confined space of the ureter, urinary bladder or biliary tract.

It is a further object of the present invention to provide for a method for affecting the destruction and removal of calculi utilizing the novel combination device described herein.

It is a yet further object of the present invention to provide a safe and efficient method for affecting the destruction and removal of calculi from the human ureter, urinary bladder or biliary tract, without subjecting the patient to the same level of risk as was heretofore experienced using available prior art devices and techniques.

These and other objects of the invention will become more apparent from the discussion below.

SUMMARY OF THE INVENTION

The present invention provides for a novel combination device for the destruction of urinary stones in the human bladder and within the individual ureters. More specifically, the present invention provides for an electrohydraulic lithotripsy basket (EHLB) which consists of multiple electrical conduit wires that act both as electrical conduits and collectively act as a grasping device.

The present invention also provides for a method for affecting the destruction and removal of calculi from the human ureter, urinary bladder, biliary tract, or other location within the body, in a manner consistent with subjecting the patient to a reduced risk of harmful complications, based upon the level of risk heretofore experienced with prior art techniques.

The construction and obvious advantages of the device and method provided for by the present invention will be more clearly understood from the following description of the various specific embodiments when read in conjunction with the accompanying drawings.

BRIEF DESCRIPTION OF THE DRAWINGS

FIG. 3 is an enlarged view of the distal tip of the embodiment of the invention shown in FIGS. 1 and 2, showing the position of the EHL probe in relation to the connecting basket wire;

FIG. 4 is an enlarged view of the handle of the embodiment of the invention depicted in FIGS. 1 and 2 showing the slide clamping mechanism and the most proximal tip which serves as the point of electrical connection for a electrohydraulic lithotripsy unit; and FIG. 4A is a cross-sectional view along the line 4A—4A in FIG. 4.

DETAILED DESCRIPTION OF THE INVENTION

The present invention is directed to a novel combination device for the destruction of urinary stones in the human bladder and within the individual ureters. More specifically, the present invention is directed to an electrohydraulic lithotripsy basket (EHLB) which consists of multiple electrical conduit wires that act both as electrical conduits and collectively act as a grasping device.

Figure 1:
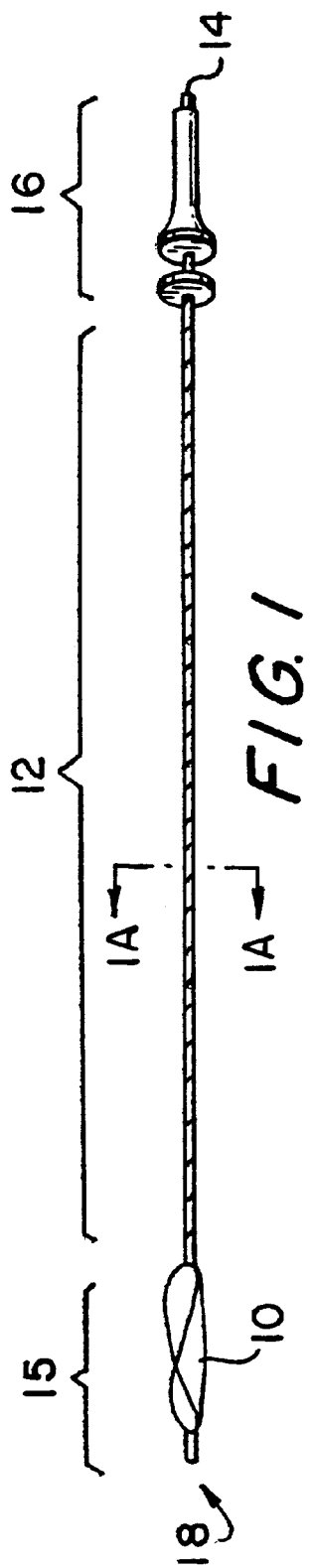
FIG. 1 is a prospective view of an embodiment of the EHLB combination device of the present invention in the open position.
Figure 1A:
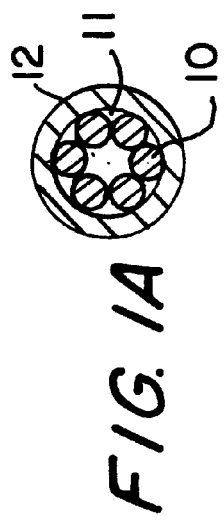
FIG. 1A is a cross-sectional view across the line 1A—1A in FIG. 1.
Figure 2:
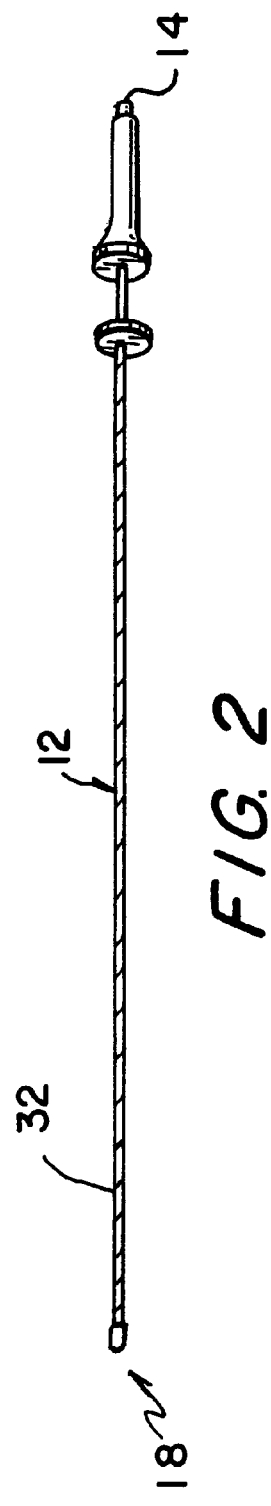
FIG. 2 is a prospective view of the embodiment of FIG. 1 in the closed position.

With reference to FIGS. 1 and 2, which depict prospective views of the EHLB combination device of the present invention in the open and closed positions, respectively, and FIG. 1A, a cross-sectional view, a multiplicity of electrical conductive wires 10 traverse an inner lumen 11 of a catheter 12. The number, length and diameter of the wires 10 will depend upon the dimensions of the working channel of the commercial cystoscope or urethroscope employed. The proximal portions of the electrical conductive wires 10 are joined in a twisted fashion, preferably clockwise, and secured at proximal base 14, which base 14 is secured within a handle 16 which permits the user to open and close the device using one hand. The distal portions of conductive wires 10 form a wire basket 15.

With reference to FIG. 3, which depicts an enlarged view of the distal end of the EHLB combination device of the present invention, the distal ends 20 of the wires 10 which form wire basket 15 converge in a single, non-traumatic metal tip 18. Tip 18 is tapered to form a round, bullet-shape at the most distal end 19. The distal wire ends 20 are attached to the proximal surface 21 of rounded tip 18. Located within the circular structure or basket 15 is a projecting EHL probe point 22 extending in the proximal direction.

Tip 18 is preferably coated with an electrical insulating lacquer except for EHL probe point 22. The wires 10 are coated with an electrical insulating lacquer in their entirety but for the proximal portion of base 14, which acts as an electrical connection to a commercial EHL device (not shown).

An enlarged view of the handle of the EHLB combination device of the present invention can be seen in FIG. 4. Handle 16 comprises catheter attachment member 28 and slide clamping member 24. Catheter or conduit 12, which is affixed to attachment member 28, comprises tubular member 27 having lumen 29. Tubular member 27 extends into lumen 30 of slide clamping member 24, and twisted wires 10 extend proximally through lumen 29 and through lumen 30 to form base 14. Base 14 is secured to the proximal portion of member 27 so that when members 24 and 28 are moved closer together, the distal portion of wires 10 extends beyond the distal portion 32 of catheter 12 to form basket 15.

The entire device may be constructed in a number of sizes and lengths, so as to be able to pass through the various sizes of working channels of commercial cystoscopes, ureteroscopes or endoscopes.

Generally speaking, the overall length of the device depicted in FIGS. 1 and 2 will be from about 100 to about 200 cm. Lengths of from about 110 to about 150 cm are also contemplated. Shorter or longer overall lengths are also contemplated as may be required to effect a particular procedure.

The overall diameter of the cross-section of the EHLB tip depicted in FIGS. 1 through 3 will be from about 1 mm to about 10 mm. It is contemplated that similar devices may be constructed having overall diameters of the tip portion which are in the range from about 1 mm to about 5 mm. It will be understood that the diameter of the tip will in use be small enough to accommodate any working channel through which the device of the invention is used.

The individual electrical wires 10 of the device depicted in FIGS. 1 through 4 will each have a diameter of from about 0.1 to about 1 mm. Electrical conductive wires having cross-sectional diameters of from about 0.2 to about 0.8 mm are also contemplated. The diameters of the wires may vary from wire-to-wire and/or along the lengths of each wire.

The materials of construction of the electrical conductive wires may be any suitable material which provides good electrical conductivity and is inert to the conditions within the human bladder or ureters as will be apparent to one skilled in the art. It is contemplated that for most applications, the electrical conducting wires will be fabricated from any conventional material, such as copper or a copper alloy.

The overall physical dimensions of the EHLB handle depicted in FIG. 4 are not critical and will be normally made in various overall lengths and configurations to comfortably accommodate the various sized hands of the users of these devices.

The base 14 is connected to any one of the commercially available EHL generators. Such generators include, for example, Model 27080 from Karl Storz and Model 2137 from Richard Wolf.

The procedure for most effectively utilizing the device of the present invention is as follows:

Under sterile conditions a cystoscope, ureteroscope or endoscope is passed into the area of interest by a trained professional. The stone is visualized. With direct vision and fluoroscopic control the EHLB is advanced in the closed position past the stone. Once past the stone, the basket is moved to the open position by the hand control. The entire unit is then gently retracted until the stone is engaged in the basket. Once the stone is engaged in the basket, the basket is closed around the stone by means of the hand control.

Once the stone is secured, the electrode is connected to a commercial electrohydraulic lithotripsy unit (EHL). The urologist or gastroenterologist is then free to activate the EHL unit while maintaining a steady amount of tension on the handle. As the stone begins to break, small pieces fall through the basket while the larger pieces are retained for further shock wave treatments. When the handle is in the original starting position the stone has been shattered and the process of snaring the tiny pieces begins. The same probe can be used to snare and extract the small pieces.

The process of engaging the stone in the basket of the device of the present invention and activating the EHL unit may be repeated as often as necessary in order to effectively shatter all of the larger pieces of the stone and to reduce them into small enough particles to allow for easy extraction or passage.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

I claim:

1. A device comprising in combination a basket extraction portion and an EHL probe, wherein the device is suitable for insertion into a body and is capable of securing a stone or calculus in a wire basket and then applying the destructive forces of the EHL probe to shatter the stone or calculus, and wherein, said basket extraction portion is comprised of a multiplicity of wires at least one of which is an electrically conductive wire which act both as electrical conduits and collectively act as a grasping device, said wires converging at the distal end of said device in a single, non-traumatic metal tip, said EHL probe having a probe point located within the circular structure of the said basket and extending in the proximal direction.

2. The device of claim 1, wherein the basket extraction portion of the device is comprised of at least two electrically conductive wires and wherein said wires traverse the inside of a catheter, are joined in a twisted fashion, and are secured at the proximal end in a base.

3. The device of claim 1, wherein the basket extraction portion of the device is comprised of at least one electrically conductive wire, wherein each said wire traverses the inside of a catheter and is secured at the proximal end in a base, and wherein the base is secured with a handle which can be operated with one hand to open and close the device.

4. The device of claim 1, wherein the metal tip is tapered to form a round, bullet-shape at its distal end.

5. The device of claim 1, wherein the metal tip has a proximal surface and an electrically conductive member extends in the proximal direction from the proximal surface.

6. The device of claim 3, wherein the handle has a proximal tip that functions as the point of electrical connection to an electrohydraulic lithotripsy unit.

7. The device of claim 1, wherein the overall length of the device is from about 100 cm to about 150 cm.

8. The device of claim 1, which can be inserted into a human bladder, urinary tract, or biliary tract.

9. In a method for destroying and removing a stone or calculus from the body wherein a longitudinally extending device has proximal and distal ends, the distal end of the device is advanced distally through a corporeal lumen to a position adjacent to the stone or calculus, and the stone or calculus is dislodged or removed, the improvement which comprises using a device according to claim 1.

10. A method for destroying or removing a stone or calculus which comprises:
   (a) advancing a device of claim 1 distally in a closed position through a cystoscope, ureteroscope, or endoscope into an area of interest;
   (b) activating the handle to open the basket;
   (c) gently retracting the entire device proximally until the stone or calculus is engaged in the open basket;
   (d) activating the hand control to close the basket around the stone;
   (e) activating an electrohydraulic lithotripsy unit (EHL) to cause the stone or calculus to shatter while a steady amount of tension is maintained on the handle to firmly secure the stone or calculus; and
   (f) repeating steps (b) to (e) as required to effect the total shattering of all of the larger pieces of stone or calculus which remain to reduce them to particles small enough for easy extraction or passage.

11. The method of claim 10, wherein the electrode at the proximal end of the device is connected to an EHL unit prior to step (e).

12. The method of claim 10, wherein the device is advanced in step (a) with direct vision and with fluoroscopic assist.

13. A device for removing a stone or calculus from a patient's body which comprises:
   a basket extraction portion comprising a multiplicity of wires at least one of which is an electrically conductive wire; and
   an EHL probe comprising a catheter having a lumen and having proximal and distal ends,
   wherein the basket extraction portion is adjacent said probe distal end, said probe distal end terminating in a probe point located within the circular structure of said basket extraction portion and extending in the proximal direction, said probe proximal end terminates in a handle, and each said electrically conductive wire from the basket extractive portion transverses the catheter lumen and is secured in the handle.

14. The device of claim 13, wherein two or more electrically conductive wires which form the basket extractive portion converge distally to form a single metal tip.

15. The device of claim 13, wherein the basket extraction portion of the device is comprised of at least two electrically conductive wires and said wires are joined in a twisted fashion and are secured at the proximal end in a base.

16. The device of claim 13, wherein the handle can be operated with one hand to open or close the device.

* * * * *